(12) United States Patent
Van Der Saag et al.

(10) Patent No.: US 11,304,967 B2
(45) Date of Patent: Apr. 19, 2022

(54) COMPOUNDS AND COMPOSITIONS FOR IMPROVING POWER OUTPUT AND OXYGEN EFFICIENCY

(71) Applicant: BIOACTOR BV, Maastricht (NL)

(72) Inventors: Antonie Johannes Van Der Saag, Maastricht (NL); Sam Possemiers, Maastricht (NL)

(73) Assignee: BIOACTOR BV, Maastricht (NL)

( * ) Notice: Subject to any disclaimer, the term of this patent is extended or adjusted under 35 U.S.C. 154(b) by 120 days.

(21) Appl. No.: 15/548,369

(22) PCT Filed: Feb. 11, 2016

(86) PCT No.: PCT/EP2016/052890
§ 371 (c)(1),
(2) Date: Aug. 2, 2017

(87) PCT Pub. No.: WO2016/128503
PCT Pub. Date: Aug. 18, 2016

(65) Prior Publication Data
US 2018/0028546 A1 Feb. 1, 2018

(30) Foreign Application Priority Data

Feb. 11, 2015 (EP) .................................... 15154689
Oct. 15, 2015 (EP) .................................... 15190026

(51) Int. Cl.
*A61K 31/7048* (2006.01)
*A61K 31/353* (2006.01)
*A61K 9/00* (2006.01)

(52) U.S. Cl.
CPC ........ *A61K 31/7048* (2013.01); *A61K 9/0053* (2013.01); *A61K 31/353* (2013.01)

(58) Field of Classification Search
CPC . A61K 31/7048; A61K 31/353; A61K 9/0053
See application file for complete search history.

(56) References Cited

U.S. PATENT DOCUMENTS 6,528,042 B1 * 3/2003 Brown ..................... A61K 8/44
424/401

FOREIGN PATENT DOCUMENTS

| EP | 2208498 | 7/2010 |
|---|---|---|
| EP | 2241313 | 10/2010 |
| JP | 2008074838 | 4/2008 |
| WO | WO 2013/144267 | 10/2013 |

OTHER PUBLICATIONS

PubChem (https://pubchem.ncbi.nlm.nih.gov/compound/Hesperetin#section=3D-Conformer; pp. 1-44; downloaded on Sep. 2, 2021).*

Myburgh, "Polyphenol Supplementation: Benefits for Exercise Performance or Oxidative Stress?" Sports Med, 2014, 44 (Suppl 1):S57-S70.
Peternelj et al., "Antioxidant Supplementation during Exercise Training, Beneficial or Detrimental?" Sports Med, 2011, 41(12): 1043-1069.
Aptekmann et al., "Orange juice improved lipid profile and blood lactate of overweight middleaged women subjected to aerobic training", Maturitas, 2010, 67(4):343-347.
Editor, "Hesperidin: Bioavailability Challenges", Biofoundations. org, 2015, XP002756487, retrieved from the Internet: URL:http://biofoundations.org/?p=2421&print=1.
Greger, "Reducing Muscle Fatigue with Citrus", nutritionfacts.org, 2013, XP002738927, retrieved from the Internet: URL:http://nutritionfacts.org/video/reducing-muscle-fatigue-with-citurs/.
Jeong et al., "Hesperidin promotes MyoD-induced myogenic differentiation in vitro and in vivo", British Journal of Pharmacology, 2011, 163(3): 598-608.
Malaguti et al., "Polyphenols in Exercise Performance and Prevention of Exercise-Induced Muscle Damage", Oxidative Medicine and Cellular Longevity, 2013, 2013, 825928, pp. 1-10.
Meletis et al., "Optimizing Wellness for Peak Physical Performance", Alternative & Complementary Therapies, 2003, 9(1): 5-10.
Nielsen et al., "Bioavailability Is Improved by Enzymatic Modification of the Citrus Flavonoid Hesperidin in Humans: A Randomized, Double-Blind, Crossover Trial", The Journal of Nutrition, 2006, 136(2): 404-408.
De Oliveira et al., "Hesperidin associated with continuous and internal swimming improved biochemical and oxidative biomarkers in rats", Journal of the International Society of Sports Nutrition, 2013, 10(1):27.
Rizza et al., "Citrus Polyphenol Hesperidin Stimulates Production of Nitric Oxide in Endothelial Cells while Improving Endothelial Function and Reducing Inflammatory Markers in Patients with Metabolic Syndrome", Journal of Clinical Endocrinology & Metabolism, 2011, 96(5): E782-E792.
Senthamizhselvan et al., "Diosmin pretreatment improves cardiac function and suppresses oxidative stress in rat heart after ischemia/reperfusion", European Journal of Parmacology, 2014, 736:131-137.
Silambarasan et al., "Diosmin, a bioflavonoid reverses alterations in blood pressure, nitric oxide, lipid peroxides and antioxidant status in DOCA-salt induced hypertensive rats", European Journal of Parmacology, 2012, 679:81-89.
Yamada et al., "Bioavailability of Glucosyl Hesperidin in Rats", Bioscience Biotechnology Biochemistry, Japan Society for Bioscience, Biotechnology, and Agrochemistry, 2006, 70(6): 1386-1394.
Salden, B. N. H., et al., Nutritional interventions focusing on gastrointestinal and metabolic health, PhD Thesis, Maastricht University, 2017, https://doi.org/10.26481/dis.20170317bs.

* cited by examiner

*Primary Examiner* — Pancham Bakshi
(74) *Attorney, Agent, or Firm* — James S. Keddie; Bozicevic, Field & Francis LLP

(57) ABSTRACT

The present invention provides the use of a compound of formula I, and compositions comprising such a compound, for improving power output and/or oxygen efficiency in a subject.

7 Claims, 3 Drawing Sheets

COMPOUNDS AND COMPOSITIONS FOR IMPROVING POWER OUTPUT AND OXYGEN EFFICIENCY

CROSS-REFERENCING

This application is the national phase under 35 U.S.C. § 371 of International Application No. PCT/EP2016/052890, filed on Feb. 11, 2016, which claims benefit of priority to European Application No. 15154689.2, filed on Feb. 11, 2015, and European Application No. 15190026.3, filed on Oct. 15, 2015, which applications are incorporated by reference herein.

FIELD OF THE INVENTION

The invention relates to the use of a compound of formula I, such as hesperitin-7-rutinoside 2S, for improving power output and/or oxygen efficiency in a subject, such as an animal or a human.

BACKGROUND

Guidelines for a healthy lifestyle comprehend the engagement in regular physical activity due to its beneficial effect on weight management and body composition. Subsequently, evidence shows a reduced risk in pathological conditions such as cardiovascular disease, type II diabetes, metabolic syndrome, and neurodegenerative diseases. Therefore people start increasing their physical activity to pursue a healthy lifestyle. The process of physical activity requires the use of oxygen to generate energy by the electron transport mechanism in the mitochondria in order to promote muscle contraction.

For many years, physical activity has been promoted as an important aspect of a healthy lifestyle. Especially professional athletes want to balance their physical activity level to improve exercise performance and reduce the likelihood of injuries. It is also known that elderly subjects lack exercise because of a sedentary lifestyle, insufficient strength to start moving and lack of endurance. The latter elements are also referred to as 'locomotive syndrome'. Especially developments in food industry have been of growing interest, since studies identified many food ingredients that could have a potential effect on exercise performance, locomotive syndrome and recovery.

For professional athletes it is common practice to consume dietary supplements to improve exercise performance and recovery. The sports nutrition market has a large offer of supplements containing antioxidant substances in order to reduce oxidative stress. During exercise $VO_2$ increases up to 20 times above normal values, which translates to a major increase of oxygen usage by the mitochondria. Due to mitochondrial inefficiency, ROS production increases as a consequence of elevated exercise, inducing oxidative stress. This mechanism has been hypothesized as a contributing factor to muscle fatigue and reduced performance. For this reason, many studies aimed at substantiating an antioxidant therapy to reduce oxidative stress and eventually improve exercise performance. Metabolic endpoints were used to conceive the effect of antioxidant supplementation on muscle damage. Although the hypothesis seems promising, result were less convincing. There are reports available showing that antioxidant supplementation my offer some protection from exercise induced cell damage and attenuation of the inflammatory response. Nonetheless, contradicting results were reported as well showing no significant effect of antioxidants on indices of cell damage, muscle soreness, and inflammation (Peternelj and Coombes, Sports Medicine 2011, 41:1043-69). Besides these studies that investigated the effect of antioxidant supplementation on markers of oxidative stress, research also aimed at the ergogenic potential of certain polyphenols. Instead of using whole fruits, studies investigate the effect of fruit extracts since these contain higher concentrations of polyphenols. For example, administration of litchi fruit extracts, containing procyanidins and proanthocyanidins enriched with catechins and epicatechins extracted from green tea, was studied for its effect on $VO_2$ during exercise. The study reported no significant effects of the extract compared to a placebo treatment. Labonté et al. (Sports 2013, 1:55-68), investigated the acute effects of polyphenols from cranberries and grape seeds on endothelial function and performance in elite athletes. Results showed an improvement in endothelial function, although no effects were found regarding performance during a three-kilometer time-trail. In contrast, a review by Malaguti et al. (Oxid Med Cell Longev 2013, Art 825928) reports positive effects of polyphenols on exercise performance and recovery. These findings represent an ongoing inconsistency caused by major methodological differences in population base and endpoints used (Myburgh, Sports Medicine 2014, 44:57-70). It seems that certain polyphenols possess interesting effects when administered to participants as sports nutrition, although results are still inconclusive.

Besides developments in performance enhancing ingredients, research aims at exercise recovery as well, which is an important aspect of athletes' performance. Today, many products aim at restoring glycogen levels and improving muscle anabolism by developing product formulations containing carbohydrates and proteins. Both food components have shown to increase muscle recovery following high intensity-training by a broad range of studies. Although positive results have been obtained, these products seem to have little applications in endurance trained athletes. Therefore, other nutritional components have gained attention for their potential effect on exercise recovery. US20110123653A1 describes the effectiveness of polymethoxylated flavone (PMF) compounds in decreasing the timespan, for subjects who engaged in exercise, for returning to basal oxygen consumption. Literature suggest an increase of total antioxidant capacity following PMF administration in horses, thereby affecting the level of muscle damage. As already mentioned, research has been inconclusive in studying the correlation between exercise performance/recovery and antioxidant status.

Thus, there remains a need for identifying novel compounds, preferably food grade and from natural origin, to improve exercise performance, locomotive syndrome and recovery. In particular, there remains a need to improve oxygen consumption/efficiency, for example allowing a subject to increase power output for the same level of consumed oxygen.

SUMMARY OF THE INVENTION

It has surprisingly been found that compounds such as hesperidin, its aglycone form hesperitin and close analogues and derivatives thereof increase power output in subjects. In addition, they improve oxygen consumption in subjects. In particular, they can be used for lowering the ratio of oxygen consumption over power output. Therefore, in a first aspect, the invention provides the use of a compound of formula I

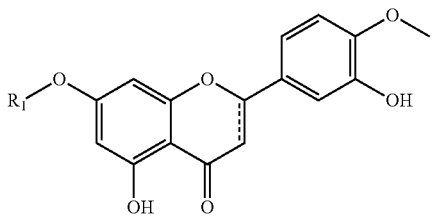

wherein
R₁ is hydrogen or a saccharide consisting of 1 to 5 monosaccharide units; and
--- represents a single or double bond;
for increasing power output in a subject.

In a second aspect, the present invention provides the use of a compound of formula I as defined above for improving oxygen efficiency in a subject. In a further embodiment, the present invention provides the use of a compound of the invention for increasing power output while maintaining or lowering oxygen consumption.

Hesperitin-7-rutinoside is a member of the flavanone glycosides, which has been studied for its effect on cardio metabolic function. Evidence shows that the compound has both antioxidant effects as well as positive effects on endothelial function. Rizza et al. (J Clin Endocrinol Metab 2011, 96:E782-792) identified the NO stimulating effect of hesperidin in Bovine Aortic Endothelial Cells (BAEC). A subsequent clinical trial showed improvements in flow mediated dilation (FMD) in metabolic syndrome patients, indicating a positive effect on endothelial function. Wilmsen et al. (J Agric Food Chem 2005, 53:4757-61) demonstrated a strong reduction in oxidative damage in cells pre-treated with hesperidin, elucidating the strong antioxidant capacity of the flavanol compound. Jeong et al. (British Journal of Pharmacology 2011, 163:598-608) identified that hesperidin promotes myogenic differentiation of myoblast cells and accelerates muscle regeneration induced by freeze injury. None of the prior art references teaches or even suggests that hesperidin and analogues may improve oxygen consumption.

Hesperidin (also referred to herein as hesperitin-7-rutinoside) is a flavonoid, specifically a flavanone, which is commonly found in several plants, including citrus fruits (e.g. oranges, grapefruit) and roots from valerian species. Here, the compounds described herein for use in the invention may originate from any plant and may refer to any of the following: the native glycoside hesperidin, as well as partially deglycosylated forms, the aglycon form hesperitin, and farther metabolized derivatives that can result from bacterial digestion, intestinal uptake, and hepatic metabolism. They may further comprises any chemically or enzymatically derived derivative of any of the foregoing molecules.

Hesperitin-7-rutinoside after extraction without enantiomeric enrichment, is a mixture of an R- and S-anantiomers, the R:S molar ratio of which is between 1:1 and 1:5, depending on its source. A mixture of R- and S-enantiomers which has a molar ratio of 1;1 is also known as a racemic mixture. Hesperidin may refer to racemic hesperidin, preferably to enantiomerically enriched hesperidin, more preferably hesperidin which is enantiomerically enriched in (2S)-hesperidin. With 'enantiomerically enriched' is meant that the hesperidin has an excess of one enantiomer over the other. Enantiomeric enrichment can be achieved amongst other methods known by a person skilled in the art by selection of the botanic source of hesperidin, and/or stereochemical separation techniques, such as capillary electrophoresis (CE). In a particular embodiment, the present invention provides the use (supra) of a composition according to the invention, wherein said composition is enantiomerically enriched for formula II

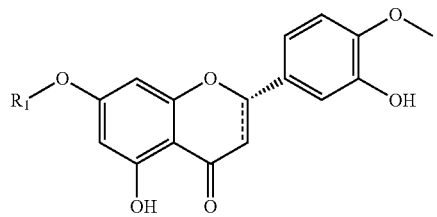

wherein R₁ is as defined herein.
In a further embodiment, it provides a composition that is enantiomerically enriched for formula IIa

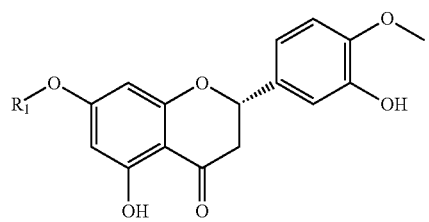

wherein R₁ is as defined herein.

The term 'physical activity' as used herein, refers to as any bodily movement produced by skeletal muscles that require energy expenditure. Active muscle tissue requires a continuous supply of energy (ATP) for maintaining cell integrity and function. As such, muscle fibers can be distinguished according to their metabolic capacity and physiological functioning. Therefore, different fiber types are more dominantly dependent on the type of exercise. Type I fibers are more active during aerobic exercise and contain a higher density of mitochondria to generate energy in the presence of oxygen. In contrast, type IIa and IIb are activated during anaerobic exercise and therefore contain a lower density of mitochondria.

The terms 'anaerobic' and 'aerobic' exercise refer to the generation of energy in respectively the absence or presence of oxygen. 'Anaerobic exercise' as used herein, refers to energy metabolism in the absence of oxygen, causing an increase in anaerobic metabolites. These metabolites, mainly lactate, have been proposed to be a main initiator of muscle fatigue and soreness.

'Aerobic exercise' as used herein, refers to energy metabolism in the presence of oxygen, mainly activated during low or moderate intensity exercise. Aerobic capacity has shown important implications in long-term endurance exercise, since the occurrence of muscle fatigue is reduced compared to anaerobic exercise.

The terms 'performance' and 'exercise performance' refers to movements of a subjects that can be maintained for the duration of an exercise to achieve a desired result of strength, speed, stamina, power, precision or metabolic output. In certain embodiments, exercise performance refers to an increase in work load, increased stamina, and so forth.

Overall, performance refers to the amount of output that can be generated within a time limit or before reaching fatigue.

The term 'short-term exercise performance' as used herein, refers to performance generated in a short period of time, in which mainly anaerobic energy is been generated. Short-term performance comprises the maintenance of high intensity exercise for a certain duration to achieve a desired result. In certain embodiments, an increase in short-term exercise performance can be measured as a higher power output, increased stamina, number of repetitions before reaching fatigue. In some embodiments, an increase in performance is an increase in velocity generated, e.g. during running, or increasing distance covered before reaching fatigue.

The term 'long-term exercise performance' or 'endurance performance' as used herein, refers to performance generated for a longer period of time, in which mainly aerobic energy is being generated. Endurance performance is characterized by low to moderate intensity exercise whereby fatigue is postponed compared to short-term exercise. In certain embodiments, an increase in endurance exercise can be measured by work load, distance covered, speed generated, repetitions, increased stamina, and number of repetitions before reaching fatigue.

Exercise performance also affects physiological parameters, which can be used as a measure in determining the effects of exercise on performance. For instance, increased performance could result in an increase of fat metabolism, lactate production, increased heart rate, and increased ventilation. Therefore, physiological parameters can be used as a measure of performance, which can be affected by performance enhancing strategies.

'Exercise recovery' as used herein, refers to a post-exercise period in which performance is influenced by prior physical activity. Exercise recovery can be defined by three types of recovery respectively 'immediate recovery', 'short-term recovery', and 'training recovery'. Immediate recovery refers to recovery occurring between rapid, time-proximal finite efforts. 'Short term recovery' refers to recovery between interval activities, e.g. sprints or weight training sets. Finally, 'training recovery' refers to recovery between successive work-outs or competitions, e.g. following a football match (Bischop et al. The Journal of Strength and Conditioning Research 2008, 22:1015-24).

The term 'muscle soreness' as used herein, refers to experienced pain inflicted by physical exercise. Muscle soreness can be divided into 'immediate muscle soreness' and 'delayed onset muscle soreness (DOMS)'. Immediate muscle soreness is characterized by soreness perceived immediately after participating in exercise involving muscle stiffness, aching pain, and/or muscular tenderness. These symptoms are relatively transient since DOMS symptom onset is about 24 hours following exercise, with a peak within 72 hours and eventually disappearing in 5 to 7 days. Several mechanism have been identified as possible initiators of muscle soreness involving lactic acid, muscle spasm, connective tissue damage, muscle damage, inflammation, and enzyme efflux theories. The onset of muscle soreness does not involve a single mechanism, but it is characterized by multiple physiological and biomechanical processes (Lewis et al. Clinics in Sports Medicine 2012, 31:255-62).

The term '$VO_2$' as used herein, refers to a volume of oxygen uptake that is used by the body for physiological processes such as energy metabolism. Dependent on exercise intensity, $VO_2$ may increase or decrease to meet the required amount of oxygen for prolonging exercise. Improving oxygen efficiency could reduce $VO_2$ necessary to achieve a certain target. Therefore, improving oxygen efficiency by training or nutrition could prolong exercise by postponing maximal oxygen utility, the $VO_{2max}$.

'Improving oxygen efficiency' refers to reducing the amount of oxygen required for physical activity. In a particular embodiment, the use according to the present invention results in a lower use of oxygen to produce 1 watt, compared to the oxygen needed for producing 1 watt in the control group. Thus, in said embodiment, 'oxygen efficiency' refers to the ratio of oxygen needed for producing 1 watt of power. In other words, the use according to the present invention lowers the ratio of oxygen consumption over power output in a subject.

'Locomotive syndrome' refers to the syndrome in elderly that makes them dependent on nursing care services. Locomotive syndrome may be diagnosed according to the Japanese Orthopaedic Association guidelines (Guidebook on locomotive syndrome. Tokyo: Bunkodo; 2010).

DETAILED DESCRIPTION OF THE INVENTION

Figure 1:
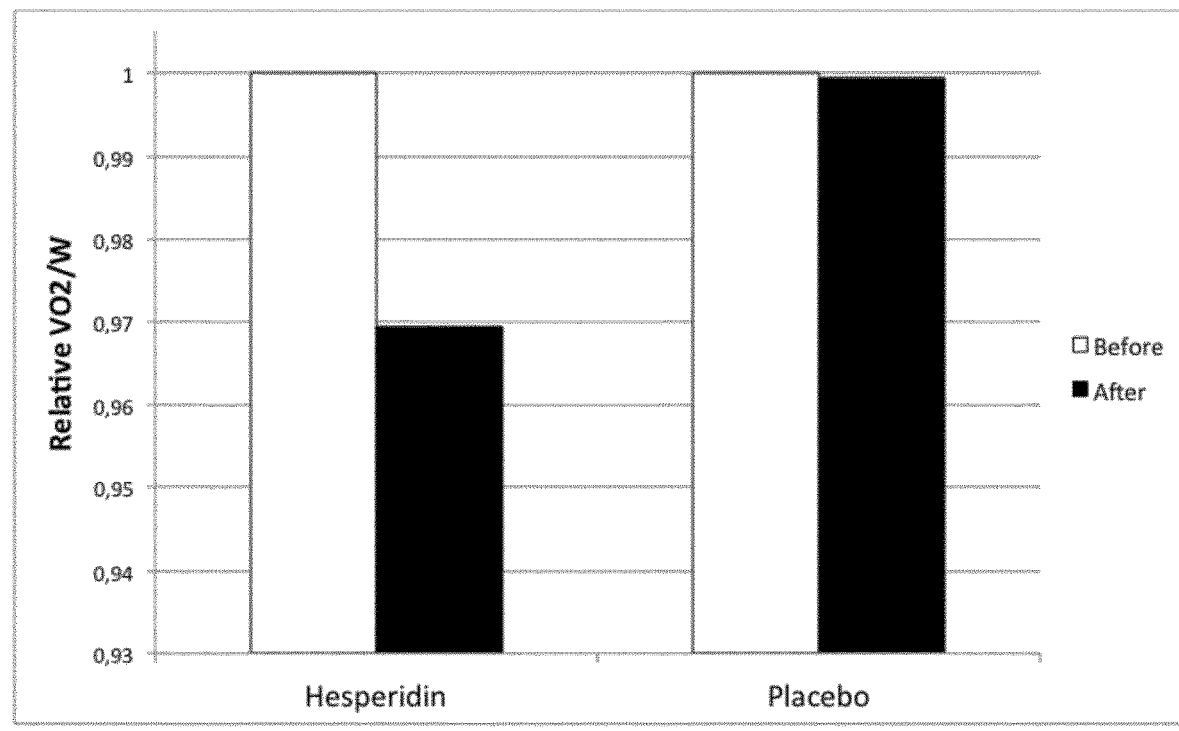
FIG. 1 shows the relative $VO_2$ over power ratio in the hesperidin and control group. Empty and full bars show relative values before and after hesperidin treatment, respectively.

Until now the use of the compounds of formula I have not been known to have any effect on power output and/or oxygen efficiency.

As described herein before, the present invention provides compounds of formula I for use in increasing power output and/or improving oxygen efficiency in a subject. In a further particular embodiment, the present invention provides a compound of formula Ia

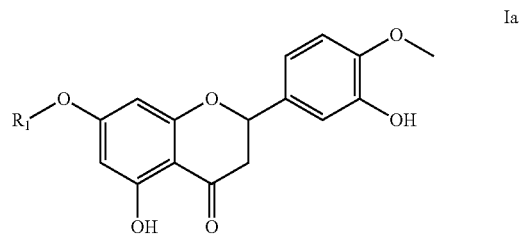

for use of the present invention, wherein $R_1$ is as defined for a compound of formula I.

In a preferred embodiment, $R_1$ as present in the compounds described herein, is hydrogen or a saccharide consisting of 1 to 5 rhamnose and/or glucose units; in particular 1 to 3; more in particular 1 or 2 rhamnose and/or glucose units. In a further preferred embodiment, $R_1$ is rhamnoglucosyl; more in particular said compound is hesperidin. In another particular embodiment, $R_1$ is hydrogen; more in particular said compound is hesperitin. In another particular embodiment, $R_1$ is glucosyl; more in particular said compound is hesperitin 7-glucoside, e.g. as described in Nielsen et al. (J Nutr 2006, 136:404-408). In yet another particular embodiment, said compound is glucosyl hesperidin, e.g. as described in Yamada et al. (Biosci Biotechnol Biochem 2006, 70:1386-94).

In another particular embodiment, the compounds for use of the present invention are selected from hesperidin, diosmin, and neohesperidin, or their aglycon forms hesperitin neohesperitin, and diosmetin. In a further embodiment, said compound is hesperidin or hesperitin, in particular hesperidin.

In the preferred embodiment, hesperidin is extracted from peels derived from sweet oranges (immature dried fruit). An extracted liquid is retrieved following alkaline extraction. This liquid is treated with sulfuric acid ($H_2SO_4$) to obtain hesperitin-7-rutinoside 2S, which is eventually treated with a mixture of $H_2SO_4$ and sodium hydroxide (NaOH) to obtain the finished hesperitin-7-rutinoside 2S.

In a particular embodiment, present invention provides a compound or composition of the invention for lowering the ratio of oxygen consumption over power output in a subject. In a further embodiment, the ratio is lowered by increasing power output while maintaining or lowering oxygen consumption. In a preferred embodiment, the ratio is lowered by increasing power output and maintaining oxygen consumption.

In a particular embodiment, the subject is a mammal. In another particular embodiment, the subject is a human. In a preferred embodiment, the subject is a healthy subject. In another embodiment, the invention provides the non-therapeutic use of the compounds described herein. In said embodiment, the compounds are not used for therapy, i.e. for treating a disease or alleviating suffering. Rather, they are used for performance improvement, such as improving oxygen efficiency and/or power output. Such methods are particularly beneficial for subjects exercising to a state of fatigue, and subjects suffering from locomotive syndrome or intermittent claudication. In some embodiments, the subject is a trained athlete. In another embodiment, the subject is an untrained person, e.g. subjects that leads a sedentary lifestyle. In a further embodiment, the present invention provides the use of the compounds described herein for improving oxygen efficiency during physical activity.

In one embodiment, the present invention comprises a composition of hesperitin-7-rutinoside 2S that has shown to have a higher bioavailability up to 108% compared to standard hesperidin. These improvements in bioavailability is of most importance for applying this product in sports nutrition, since the effect will be more pronounced compared to standard hesperidin. To achieve improvements in exercise performance, the product should elicit an immediate response following administration.

The invention comprises a composition that reduces the occurrence of oxidative damage during exercise and improves the availability of nutrients and the efficient use of oxygen by muscle tissue. Subsequently, improving blood flow to muscle tissue reduces the transition of aerobic to anaerobic metabolism, which prolongs time to exhaustion by reducing accumulation of anaerobic metabolites.

In some embodiments, the invention comprises a method for reducing oxygen consumption during exercise, wherein the administered composition improves performance by increasing oxygen efficiency during exercise. Improvement in oxygen efficiency reduces the amount of oxygen necessary to perform at a certain physical activity level.

In another particular embodiment, the present invention provides the use of the compounds or compositions described herein for increasing the anaerobic capacity in a subject. In particular for increasing power output or peak force output during anaerobic activity.

In one embodiment, the invention comprises a method for reducing muscle soreness during and post-exercise by administering an effective composition. Muscle soreness comprehends immediate muscle soreness and DOMS, involving different processes causing the onset of muscle soreness. Improvements in muscle soreness reduction can last from minutes to hours, while DOMS lasts from days up to one week. Therefore, the present invention comprises a method for reducing muscle soreness both short- as well as long-term.

In certain embodiments, the invention comprises a method for increasing aerobic performance during exercise, by administering an effective composition comprising a compound of formula I. Improvements in oxygen efficiency positively affects aerobic performance, since less oxygen is utilized for an equal level of performance.

In certain embodiments, the invention comprises a method for improving anaerobic performance during exercise, by administering an effective composition comprising a compound of formula I for reducing muscle damage and muscle soreness induced by high intensity exercise.

Furthermore, the present invention provides the compound of formula I, Ia, II or IIa or the compositions comprising such a compound for use in the prevention and/or treatment of an impaired oxygen transport diseases; in particular the treatment and/or prevention of intermittent claudication.

In certain embodiments, the invention comprises a method for increasing (muscle) strength, particularly in elderly subjects, thus improving their mobility, by administering an effective composition comprising a compound of formula I. The invention further provides a compound of the invention for increasing muscle strength in a subject, preferably in an elder subject. An elder subject particularly refers to a subject of at least 60 years, preferably at least 65 years, more preferably at least 70 years.

Mode of Administration

Studies have shown good bioavailability of hesperidin and analogues described herein when administered orally. It is therefore an object of the invention to provide compositions comprising the compounds described herein that can be orally administered, while improving exercise performance, in particular oxygen efficiency, and recovery. Preferred compositions for oral administration include:

Sub-lingual films, tablets, or lozenges (tablets that slowly dissolve in the mouth) that ensure uptake of the compounds described herein through sublingual and/or buccal mucosa, bypassing the intestinal microflora and hepatic circulation.

Composition of orange peel extract comprising the compounds described herein, which is active when taken orally in typical dosage forms like capsules, beverages, and food products.

In a particular embodiment, the present invention provides the use of a composition comprising a compound of formula I for increasing power output and/or improving oxygen efficiency in a subject. In a particular embodiment, said composition is composition is in the form of a liquid, solution, tablet, lozenge, dissolvable film, suspension, (dietary) gel, capsule, chewable or syrup. In a preferred embodiment, the composition is in the form of a capsule. Preferably, the capsule contains from 50-500 mg, especially from 100-350 mg, more particularly from 150-300 mg or about 250 mg of the compound of formula I.

In a preferred embodiment, a composition of the invention comprises an isolated compound of the invention or the composition has been enriched for the compound of the invention. In another particular embodiment, the composition of the invention comprises a compound of the invention and a bulking agent. The bulking agent is preferably of natural origin. Examples of bulking agents suitable for the method of administration are known to the person skilled in the art. Preferably, the bulking agent is a saccharide, including mono-, oligo- and polysaccharides; in particular a sugar or natural gum. In a further embodiment, the bulking agent is selected from the below list described for pharmaceutical carriers.

The invention relates to a composition comprising a compound of formula I, wherein the composition is a pharmaceutical composition further comprising a pharmaceutically acceptable carrier. Examples of pharmaceutical carriers are known to the person skilled in the art and include but are not limited to D-mannitol, sorbitol, sucrose, galactose, cellulose, other sugars, other saccharides, other oligosaccharides and/or polysaccharides, gelatin, guar gum, Arabic gum, agar agar, xanthan gum, locust bean gum, starch, starch fragments, dextrins, British gum and any mixture thereof. Preferably, the pharmaceutical acceptable carrier is of natural origin.

In another aspect, the invention relates to a composition comprising a compound of formula I, wherein the composition is in a form suitable for sublingual and/or buccal administration, wherein the composition is in the form of a liquid solution, (disintegrating) tablet, lozenge, dissolvable film, suspension, (dietary) gel, capsule, chewable or syrup.

'Tablets' refer to a dosage form comprising a mixture of one or more active substances including inner filler substances such as, desintegrants, binding agents, lubricants, glidants, antiadherents, flavors, coloring agents etc.

'Disintegrating tablets' are tablets with a specific composition that quickly disintegrates when getting in contact with saliva in the mouth or with water. These tablets may have the same composition as regular tablets, however, added with components optimized for disintegration time, e.g. by adding desintegrants.

'Capsules' consist of a thin layer outer wall, made from a substance that dissolves in the stomach and/or intestinal fluid, e.g. gelatin, agar etc. Capsules can be filled with the active substance as a dry powder, or as a fluid consisting of different solutions etc. that contain the active ingredient.

'Syrups' are sweetened, flavored, viscose solution that contains a certain concentration of the active substance, which can be diluted into a food or drink.

'Dietary gels' refers to highly viscous aqueous solutions of active substances that may be added with flavoring and coloring agents in the presence of a gelling agent such as gelatin, agar, acacia gums and others. This mixture of components is presented as a slowly flowing or semi-solid substance.

'Lozenges' refer to hardened mixtures of the active ingredient and additional substances that slowly dissolve when getting into contact with the saliva in the mouth, elaborating a prolonged exposure of the active substance with the buccal mucosa. Lozenges often contain flavoring and sweeteners to increase palatability.

The active ingredient can be applied in any form, according to the various embodiments of the present invention. For instance, the dosage form of the active ingredient may be provided as, e.g., a powder beverage mix, beverage syrup, a liquid beverage, a ready-to-eat bar or drink product, a capsule, a liquid capsule, a tablet, a caplet, a lozenge, a chewable tablet, dissolvable film, a dietary gel, or syrup.

Therefore, in one embodiment, the invention relates to a composition comprising a compound of formula I, wherein the composition is a food, beverage, or supplement composition for a food composition, for example a nutrition bar.

In one embodiment, the invention relates to a composition comprising a compound of formula I, wherein the composition is a food, beverage, or supplement composition for a food or a beverage, for example a nutrition bar or sports drinks, used to improve/increase exercise performance and post-exercise recovery in preferably mammals, for example humans.

In another embodiment, the invention refers to a composition comprising a compound of formula I, wherein the composition is in a form suitable for sublingual and/or buccal administration, wherein the composition is a food, beverage, or a supplement composition for a food or a beverage, for example a nutrition bar.

In one embodiment, the invention refers to a composition comprising a compound of formula I for the manufacture of nutritional products or supplements used in sports nutrition to improve exercise performance, including improvements in oxygen efficiency, in time to fatigue and physical parameters, and to improve post-exercise recovery, including improved lactate removal, reduced muscle soreness, and improvements in additional physical parameters involved in exercise recovery.

Dosages

The optimal dose of the compounds of formula I for humans, preferably human adults, can be derived using the FDA recommendations for translating to the human equivalent dose (HED) from animal studies. This recommendation translates the dosages used for animal studies to dosages per day for the general population (i.e. average human adults).

Preferably, the compound of the invention is administered (to a human adult) once daily in an amount of approximately 50-1500 mg. The ingredient is preferably administered during the morning prior to exercising.

In another particular embodiment, the present invention provides the daily administration of the compound of formula I, Ia, II or IIa in an amount of 50 mg to 1500 mg; in particular from 100 mg to 1000 mg; more in particular from 150 mg to 750 mg. In yet another particular embodiment from 400 mg to 600 mg; in particular from 450 mg to 550 mg. In another embodiment from 250 mg to 1000 mg. In a preferred embodiment, the invention provides a composition in unit dosages, wherein a compound of formula I, Ia, II or IIa is present per unit dosage in an amount as described above for daily administration.

Example 1

Study Design

In this randomized, double-blind, placebo-controlled study with parallel design, 40 participants randomly received a four weeks supplementation with either a daily dose of 500 mg hesperidin, or an identical looking and tasting placebo. The hesperidin extract was tested on its effect on exercise performance and recovery after pre-exhaustive exercise.

The study consisted of a pre-test, baseline test (Test 1) and a final test after a 4 week intervention period (Test 2). Prior to each test, participants were instructed to refrain from intense exercise and alcohol for at least 24 hours.

First a Pre-test was performed, which consisted of a ten minute time trial after a five minute warm-up at 100 W on a bike. Parameters obtained from this test were mean power, mean heart rate, mean $VO_2$-consumption and an estimation of $VO_2$-max. At t=0, 9, 10, 11 after starting the test, participants were asked to indicate their perceived exhaustion using a 10-point scale (0=lowest, 10=highest).

The mean power that was estimated during the Pre-test was used to determine the power for the 10-minute pre-exhaustion in Test 1 and Test 2. During Test 1 participants first had to cycle on 80% of the mean work-load established during the Pre-test for a duration of 10 minutes (after five minute warm-up at 100 W). During this pre-exhaustion, heart rate and exhaustion at t=0, 9, 10, 11 after starting the test were measured. In the subsequent 25 minutes the participants took complete rest and were only allowed to drink water. After these 25 minutes a 5 minute warm-up was done on 100 W and directly after that participants had to perform a 10 minute time-trial comparable with the Pre-test. The same parameters were obtained as in the Pre-test with additional exhaustion measurements at t=-2, -1 before starting the test.

After Test 1, participants received either capsules containing a daily dose of 500 mg hesperidin or 500 mg placebo in a double-blind controlled manner. After this 4 week intervention period, Test 2 was conducted for which was followed the exact same protocol as for Test 1.

Test Subjects 40 healthy non-smoking men between 18 and 25 years with a Body Mass Index between 18.5 and 25 were included. All participants were physically trained men. Physically trained was defined as 'engaged in moderate to high intensity physical activity at least three times a week for at least 30 minutes'. The average exercise time per week was 9.6 hours. Participants were not allowed to use dietary supplements or medication during the study period. Participants were asked to abide to dietary restrictions, with emphasis on avoiding consumption of citrus fruits. The study protocol was approved by the Medical Ethics Committee of Wageningen University.

Test Product

The hesperidin supplements contained >90% hesperidin. This amount corresponds to the amount of hesperidin in ca. 1.5 l of freshly squeezed orange juice. The capsules were transported and stored at room temperature. Participants were instructed to ingest two capsules with water daily before breakfast, for 4 weeks from the first morning after Test 1 until the morning of Test 2.

The capsules were packed in blisters, containing 14 capsules each. One blister therefore was enough for one week of supplementation. All participants received 4 blisters and 1 spare blister (in total 70 capsules of 250 mg).

Statistics

Statistical analysis was performed using IBM SPSS 22. Only data from participants who completed the study (n=39) were used in the analysis. The group who received hesperidin consisted of 19 participants, the placebo group consisted of 20 participants.

To determine the effects of hesperidin supplementation on the measured performance outcomes, the mean values at baseline (T1) were compared with the mean values after four weeks of supplementation (T2). A paired-samples t-test was used to compare the T1 and T2 measurements within both the hesperidin and placebo group. To compare the differences between the hesperidin and placebo group, an independent t-test was performed.

Results

Table 1 shows the results of the statistical analyses comparing the performance outcomes from the participants in the hesperidin group and placebo group, before and after the four weeks intervention period. A paired samples t-test shows that both absolute (P=0.001) and relative power (P=0.002) are significantly increased over four weeks in the hesperidin group. Since there is no difference over time in weight in both groups, performance should not be corrected for weight. Therefore we focus on the absolute power (W). In the placebo group, no significant differences are shown when comparing T2 with T1.

TABLE 1

Comparing the performance outcomes from the hesperidin group and placebo group before and after intervention

| Variable | Hesperidin supplementation (n = 19) | | | Placebo supplementation (n = 20) | | | |
|---|---|---|---|---|---|---|---|
| | Test 1 (Pre treatment) | Test 2 (Post treatment) | P1 | Test 1 (Pre treatment) | Test 2 (Post treatment) | P2 | P3 |
| Weight (kg) | 74.08 | 74.20 | 0.406 | 74.79 | 74.65 | 0.718 | 0.523 |
| Absolute power (W) | 298.04 | 312.98 | 0.001* | 300.50 | 304.31 | 0.243 | 0.032* |
| Relative power (W/kg) | 4.03 | 4.23 | 0.002* | 4.04 | 4.10 | 0.328 | 0.077 |
| Heart rate (BPM) | 169.93 | 168.73 | 0.578 | 175.81 | 177.16 | 0.206 | 0.287 |
| Average $VO_2$ (mL/kg/min) | 51.09 | 52.01 | 0.235 | 49.58 | 50.18 | 0.330 | 0.736 |
| Estimated $VO_2$ max (mL/kg/min) | 57.88 | 57.87 | 0.988 | 56.47 | 56.72 | 0.784 | 0.826 |
| $VO_2$/Power ratio | 0.171 | 0.166 | 0.001* | 0.165 | 0.165 | 0.534 | 0.001* |

P1; P-value of hesperidin group compared using a paired T-test, P2; P-value of placebo group compared using a paired T-test, P3; P-value of difference between the hesperidin and placebo group using an independent samples T-test.

Particularly surprisingly, average and estimated $VO_2$ did not differ significantly between test sessions, while absolute and relative power did increase in the hesperidin supplementation group. Thus, hesperidin administration led to strong oxygen efficiency improvements as the ratio of oxygen volume used per amount of power generated significantly decreased upon hesperidin administration (FIG. 1).

Example 2

The anaerobic capacity refers to the total amount of energy that can be obtained from anaerobic energy systems (e.g. anaerobic glycolysis). It is an important mediator of performance, especially for interval athletes. For example, 100 m sprinters are considered to fully rely on the anaerobic capacity.

Figure 2:
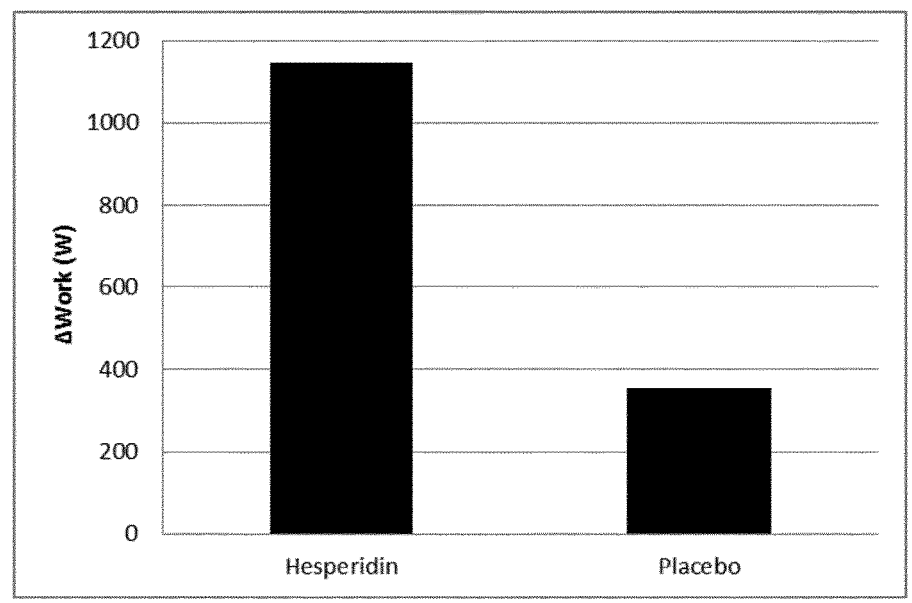
FIG. 2 shows the results of hesperidin administration on ΔWork.

An athlete was defined as an interval athlete when the sport required bursts of short-term high intensity exercise, i.e. football or 100 m sprint athletes. Anaerobic capacity was determined by measuring the total amount of work (W) generated by the test subjects over 30 seconds. Test results showed a higher anaerobic capacity for the group of interval athletes that received the hesperidin supplements compared to the control group. The anaerobic capacity difference after 4 weeks of treatment (Δ anaerobic capacity) was 3.2-fold higher in the treatment group compared to the control group (1146.8 W versus 354.6 W). Thus, as is also evident from FIG. 2, the use of a compound of the invention increases the anaerobic capacity.

Example 3

Figure 3:
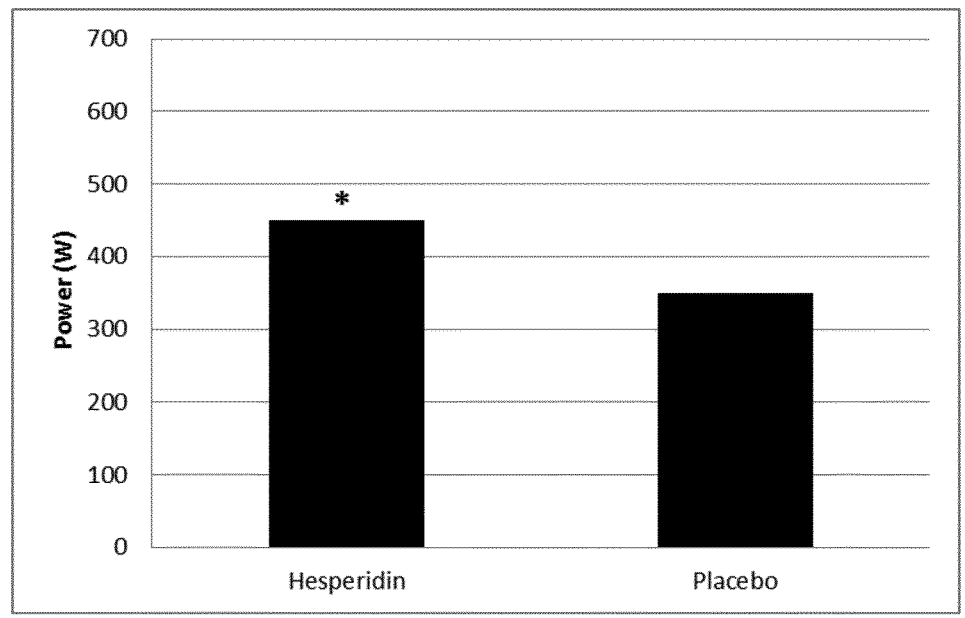
FIG. 3 shows the results on peak power output measurements in a hesperidin and control group.

Peak force capacity refers to the highest mechanical power generated in the first 3 seconds of exercise. It reflects the energy-generating capacity of high-energy phosphates and it is an important mediator of performance for resistance athletes in particular. Study design was an open-label pre-posttest study. Test product and administration were as described in example 1. The subjects of the study were resistance athletes. Peak force output was measured in a barbell squat resistance training exercise using a linear encoder. Peak force output was measured as highest amount of Force (W) generated over a single repetition of the exercise (which lasted no more than 3 seconds). Test results showed a significantly higher peak force output after 4 weeks of hesperidin supplementation for all subjects compared to baseline. Thus, as is also evident from FIG. 3 the use of a compound of the invention increases the peak force output.

Example 4

A group of elderly subjects was tested on mobility with the Timed Up & Go (TUG) assessment. Evidence has shown that mobility decreases with increasing age, partly due to a loss of muscular strength, thereby decreasing functional ability and balance, also described as the Locomotive syndrome. The TUG assessment was developed for frail elderly people in order to assess basic mobility, strength, balance and agility. It examines the time taken to rise from sitting in an armchair, walk three meters, turn, walk back to the chair and sit down again, with smaller times representing better mobility. The results show, that after receiving the test product of example 1 for four weeks, the treatment group was significantly faster in performing this exercise than the placebo group. This is mainly thought to be due to an increased peak force output and overall power in the treatment group, which have been demonstrated previously. The peak force output measures the highest mechanical power in the first 3 seconds of an exercise. In the context of this exercise, it is thought to give the test subject extra force to get up from the chair more easily and faster. Moreover, also increased overall power helps the test subjects to move faster during the task with an improved balance resulting in less time needed to complete the exercise. Thus, the compounds and compositions of the invention improve locomotion and mobility in elderly or frail subjects.

Example 5

Figure 4:
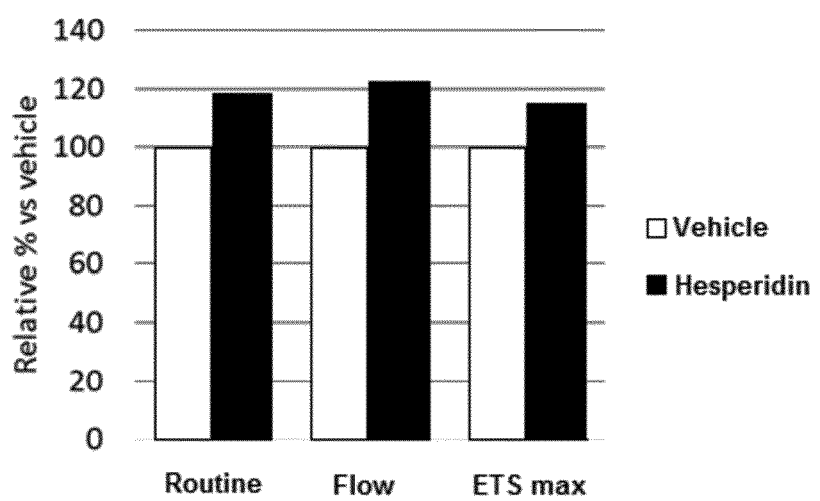
FIG. 4 Effect of hesperidin at 40 μg/mL in the basal respiration (routine), oligomycin-induced proton flow (Flow) and FCCP-induced maximal Electron Transfer System (ETS max) of horse skeletal muscle cells (myoblasts). Relative percentage versus vehicle (control) is shown for cells supplemented with vehicle (100%) and hesperidin.

By using High Resolution Oxygraphy, the effect of the active metabolites from hesperidin on mitochondrial respiration efficiency was assessed in muscle cells derived from horse skeletal muscle. This evaluated the total respiration process and specific aspects of this process linked to proton leak and electron transfer system. A clear and significant effect was shown on all aspects of mitochondrial respiration capacity upon 24 h pretreatment of the cells with hesperidin. Examples from these findings are shown in FIG. 4, confirming the potential of hesperidin to increase the energy-generating capacity of mitochondria in the muscle. Hesperidin administration increased the proton flow in the mitochondria of skeletal muscle cells. From this it can be concluded hesperidin results in a higher (H+) proton availability through preventing mitochondrial leakage. Due to this higher available quantity of H+ ions more ATP can be generated at similar levels of oxygen uptake. Therefore, without wishing to be bound by theory, it appears that hesperidin supplementation can generate more ATP per unit of oxygen consumed by reducing mitochondrial leakage, which leads to a higher energy availability for the consumer.

Example 6

In total, 11 healthy non-smoking men between 18 and 30 years with a Body Mass Index between 18.0 and 30.0 were enrolled in the study. Participants were included after signing informed consent and when was established that they met the inclusion and exclusion criteria during a screening visit. All participants were physically trained men or women. Physically trained was defined as 'engaged in moderate to high intensity physical activity at least two times a week for at least 30 minutes. All participants completed the study. Baseline characteristics of the participant population is shown in Table 2.

TABLE 2

| Baseline characteristics | |
|---|---|
| Parameter | |
| N, participants | 11 |
| Age, years | 26 ± 3.1 |
| Sex, males (%) | 7 (63) |
| Bodyweight, kg | 74.7 ± 12.0 |
| Height, cm | 178.3 ± 10.8 |
| BMI | 23.4 ± 2.2 |
| Exercise hours | 7.09 ± 4.9 |
| Supplement usage (%) | 5 (45) |

Values are means ± SDs

The hesperidin-enriched extract was formulated into capsules containing 250 mg by Aminolabs (Hasselt, Belgium). The placebo (cellulose) capsules were produced to be identical in appearance and taste. The capsules were transported and stored at room temperature. Participants were instructed to ingest two capsules with water daily before breakfast, for 4 weeks from the first morning after Test 1 until the morning of Test 2. This led to a total daily dose of 500 mg. The capsules were packed in jars, containing 56 capsules each. One jar therefore was enough for 4 weeks of supplementation. All participants received 1 jar (in total 56 capsules of 250 mg).

The study consisted of a baseline test (Test 1) and a final test after a 4 week intervention period (Test 2). Prior to each test, participants were instructed to refrain from intense exercise and alcohol for at least 24 hours. A squat exercise was performed on test days to assess exercise performance. The squat exercise is a resistance training exercise in which the musculus quadriceps femoris, musculus biceps femoris and gluteus maximus are mainly involved. In this exercise, the participant squats down by bending the hips backward, while allowing the knees to bend forward. During the exercise the back will be kept straight and the knees are pointed in the same direction as the feet. The participant descends until their thighs are parallel to floor. Once achieved the knees and hips are extended until the legs are straight. This is repeated for the designated amount of repetitions. An external load attached to a barbell was used to achieve the desired weight distribution.

The following test protocol was followed identically on both test days:

Pre-test phase: First, a one-repetition maximum (1RM) test on the squat exercise was performed, which served to assess the maximum weight a person can lift for one repetition. Through self-reported one-repetition maximum (1RM) or by calculating the circa 1RM (=bodyweight+((amount of reps*max lifted weight)*0.0333) (Epley B., Poundage chart, In Boyd Epley Workout, 1985)) the true 1RM was tested according to the following protocol:
20 repetitions at bodyweight
6 repetitions at 40% of 1RM
3 repetitions at 50% of 1RM
2 repetitions at 70% of 1RM
1 repetition at 80% of 1RM
1 repetition at 90% of 1RM
1 repetition at 100% of 1RM
A rest period of 3 minutes is taken between each set. The 1RM that was achieved during the pre-test was used to determine the load for the explosive strength test. No measurements took place during this phase. For the explosive strength test an external load of 70% of the achieved 1RM was used.

Rest phase: In the subsequent 5 minutes, the participants took complete rest and were only allowed to drinking water.

Explosive strength phase: After these 5 minutes, participants had to perform an explosive strength test. Parameters obtained from this test were average force (AF), average velocity (s) and peak force (PF) and were measured using the Linear Encoder device from MuscleLab™.

Test day 2 consisted of the exact same procedure. To account for the training-effect of athletes—it is assumed athletes improve over time because of their training—the 1RM was assessed again. The 70% 1RM on test day 2 was set according the 1RM assessed on test day 2, i.e. if the athlete achieved a higher 1RM on test day 2, a higher 70% 1RM was used for force measurement.

As depicted in table 3, Peak force (PF), peak force divided by bodymass (PF/m), average force (AF) and average force divided by bodymass (AF/m) increased significantly after 4 weeks compared to baseline (P<0.05). There were no significant differences in 1RM, 70% 1RM, S, PF/s and AF/s before and after 4 weeks.

TABLE 3

1RM, 70% 1RM, exercise speed, peak force and average force at baseline and after 4 weeks

| Parameter | Baseline | 4 wk | Δ | P |
|---|---|---|---|---|
| 1RM, kg | 101.1 ± 32.7 | 104.3 ± 29.1 | 3.2 ± 7.5 | 0.19 |
| 70% 1RM, kg | 71.4 ± 23.4 | 72.7 ± 20.1 | 1.4 ± 6.3 | 0.49 |
| S, m/s | 0.68 ± 0.08 | 0.71 ± 0.07 | 0.03 ± 0.07 | 0.11 |
| PF, W | 1095.8 ± 463.1 | 1207.8 ± 410.3 | 112 ± 128.0 | 0.02 |
| PF/m, W | 14.2 ± 4.7 | 15.9 ± 4.08 | 1.7 ± 1.9 | 0.01 |
| PF/s, W | 1558.9 ± 572.2 | 1653.7 ± 475.5 | 94.8 ± 257.4 | 0.25 |
| AF, W | 553.4 ± 251.0 | 615.7 ± 271.2 | 62.3 ± 72.3 | 0.02 |
| AF/m, W | 7.13 ± 2.4 | 8.0 ± 2.6 | 0.9 ± 0.9 | 0.01 |
| AF/s, W | 787.9 ± 304.4 | 839.7 ± 327.6 | 51.9 ± 108.0 | 0.14 |

1Values are means ± SDs.
21RM = one rep max; S = exercise speed; PF = peak force; PF/m = peak force per kg bodyweight PF/s = peak force divided by exercise speed; AF = average force; AF/m = average force per kg bodyweight; AF/s = average force divided by exercise speed.
3Calculated by using paired t-test.

Figure 5:
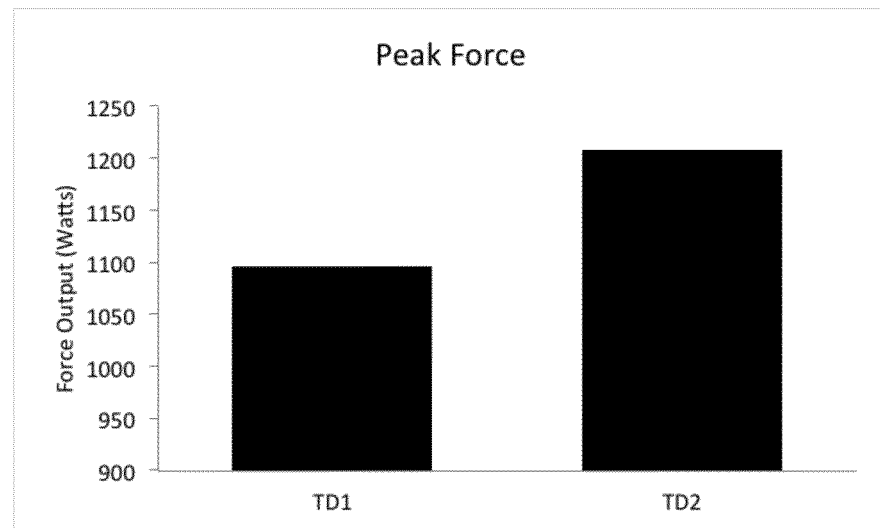
FIG. 5 Peak force output before and after treatment at test day 1 (TD1) and test day 2 (TD2). Participants show an overall increase in peak power at test day 2 compared to baseline. Peak force output increased significantly with 10.2% (p=0.02).

As shown in FIG. 5, supplementation with the composition of the invention leads to an spike in explosive power output in a single repetition high intensity resistance exercise. During this very short initial exercise period, the immediate ATP-PCr system is the main contributor to generating this power output. Intramuscular high-energy phosphates (ATP & PCr) are released for immediate energy and subsequently resynthesized. The energy to phosphorylate ADP during short-term exercise comes from stored muscle glycogen breakdown via (rapid) anaerobic glycolysis, resulting in lactate formation. This rapid glycolysis allows ATP to form rapidly without oxygen. FIG. 5 shows that the peak force output after 4 weeks of treatment is larger after treatment (1207.78 W) than before treatment (1095.78 W). Peak force output increased significantly with 10.2% (p=0.02). In addition, almost all participants increased their peak force output per kilogram body mass. The average peak force output per kilogram body mass increased from 14.2 W/kg to 15.9 W/kg, marking an 11.9% increase of peak force/kg body mass.

Figure 6:
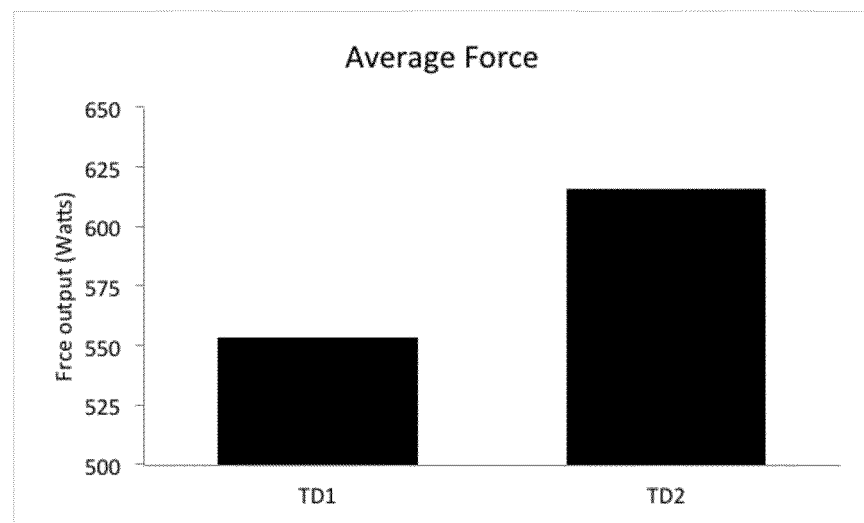
FIG. 6 Average force output before and after treatment at TD1 and TD2. Participants show an overall increase in average power at test 2 compared to baseline. Average force output increased significantly with 11.3% (p=0.02).

In addition to the peak force output the average force output over the entire concentric phase of the exercise was assessed. FIG. 6 shows that the average force output (over the entire repetition) after 4 weeks of treatment is significantly larger after treatment (615.72 W) than before treatment (553.42 W). After 4 weeks supplementation with the composition of the invention, the average force output increased by 11.3%. Furthermore, almost all participants increased their average force output per kilogram body mass. The average peak force output per kilogram body mass increased from 7.1 W/kg to 8.0 W/kg, marking a 12.2% increase of average force/kg body mass.

In short, the compositions of the invention increase strength performance in resistance-trained athletes, exemplified by causing a 10.2% and 11.3% increase in peak force output and average force output, respectively. The measured increase in peak force output and average force output per kilogram body mass confirms that this increase is not a consequence of an increase in body mass and/or muscle mass. This suggests that in the immediate energy generating system the compositions of the invention allow for more available energy.

In conclusion, PF, PF/m, AF and AF/m increased significantly after 4 weeks. There were no significant increases in 1RM, 70% 1RM, PF/s and AF/s after 4 weeks.

PF and AF increased by 10 and 11% respectively after 4 weeks of supplementation. PF/m and AF/m increased accordingly, as bodyweight remained constant after 4 weeks. This confirms that the increase in AF and PF is not a result of an increase in body mass and/or muscle mass. To further correct for the training effect the 1RM, and as a result the 70% 1RM, was assessed separately for each test day. Nevertheless, even with a higher tested weight (70% 1RM) the participants were able to increase their velocity, AF and PF in the barbell squat resistance exercise. One-RM and 70% 1RM increased after 4 weeks, but this was not statistically significant. While a slight increase in 1RM was expected it is interesting to note that the 1RM in certain participants increased by a weight of 10 kilograms. In trained individuals this is a relatively large improvement for only 4 weeks' time. It might be that the composition of the invention contributes to an increase in 1RM to a certain extent too. The results of this example further corroborate the results of example 1, which showed that 4 weeks of supplementation significantly increased the absolute power by 5% in trained athletes within the treatment group when compared to placebo. Furthermore, the peak force output increased by 36% compared to baseline in example 3. In contrast, peak force output increased by 10% in the current study. This difference may at least be partly attributed by the different study protocols. In example 3, participants had to cycle at 80% of their established mean-work load (determined by pre-test of 10 min) for 10 min, rest for 25 min, warm up for 5 min at 100 W and thereafter again cycle at 80% of established mean-work load for 10 min on both test days. In the current study, the 1RM on the squat exercise was established for each participant. They then had to rest for 5 min, and subsequently perform an explosive strength test at 70% of their 1RM. The squat is an explosive exercise only lasting a few seconds per repetition, whereas cycling is often of longer duration. Nevertheless, these examples show that the compositions of the invention have beneficial effects on different types of exercise, and can be used for a greater amount of applications.

A potential mechanism could be that the compounds of the invention have a positive effect on the ATP production in the mitochondria and that they lower levels of oxidative stress, thereby increasing energy availability in the muscle and decreasing oxidative muscle damage which ultimately increases strength output.

Summarized, the above examples convincingly show the capacity of the compositions of the invention as natural supplements for supporting athletes to maximize explosive strength performance capacity.

The invention claimed is:

1. A method for improving oxygen efficiency by lowering the ratio of oxygen consumption over power output, the ratio represented by $VO_2$/power, in a healthy subject, the method comprising administering prior to physical exercise and/or the onset of stress caused by such exercise to the subject a composition comprising hesperidin in a mixture of R- and S-enantiomers, wherein the R:S molar ratio of the mixture is between 1:2 and 1:5,
    and wherein the healthy subject is selected from a trained athlete, a moderately trained subject or an untrained subject.

2. The method of claim 1 wherein the method results in increased power output during physical activity.

3. The method of claim 1, wherein said composition is administered orally.

4. The method of claim 1, wherein the method results in increased power output while maintaining or lowering oxygen consumption.

5. The method as claimed in claim 1, wherein the mixture is administered once daily in an amount of 250-1000 mg.

6. The method as claimed in claim 5, wherein the mixture is administered once daily in an amount of 400-600 mg.

7. The method as claimed in claim 6, wherein the mixture is administered once daily in an amount of 450-550 mg.

* * * * *